United States Patent [19]

Vykoupil

[11] Patent Number: 4,615,216
[45] Date of Patent: Oct. 7, 1986

[54] METHOD OF ANTICIPATING MACHINE FAILURE

[75] Inventor: Peter Vykoupil, Moers-Schwasheim, Fed. Rep. of Germany

[73] Assignee: Rheinisch-Westfalischer Technischer Uberwachungsverein E.V., Essen, Fed. Rep. of Germany

[21] Appl. No.: 743,584

[22] Filed: Jun. 11, 1985

[51] Int. Cl.$^4$ ............................................. G01N 29/04
[52] U.S. Cl. ........................................ 73/593; 73/660
[58] Field of Search .................. 73/593, 660; 340/683

[56] References Cited

U.S. PATENT DOCUMENTS

| | | | |
|---|---|---|---|
| 3,548,648 | 12/1970 | Weichbrodt et al. | 73/593 |
| 3,793,627 | 2/1974 | Darrel et al. | 73/593 |
| 3,872,285 | 3/1975 | Shum et al. | 73/660 |
| 4,089,055 | 5/1978 | Dyer et al. | 73/593 |
| 4,213,114 | 7/1980 | Cochard | 73/593 |
| 4,425,798 | 1/1984 | Nagai et al. | 73/660 |

*Primary Examiner*—Anthony V. Ciarlante
*Attorney, Agent, or Firm*—Karl F. Ross; Herbert Dubno

[57] ABSTRACT

A method of anticipating defects in the operation of a machine, especially a rotary machine in which high-frequency and low-frequency ranges of a body-wave spectrum in a solid part of the machine are detected and respective auto-spectral density functions $G_{11}$ and $G_{22}$ are formed, the cross spectral density function $G_{12}$ being formed from the measurements as well. The magnitude $\gamma^2 = G_{12}^2/G_{11} \cdot G_{22}$ is formed and the defect is anticipated by an increase in the value of $\gamma^2$.

7 Claims, 1 Drawing Figure

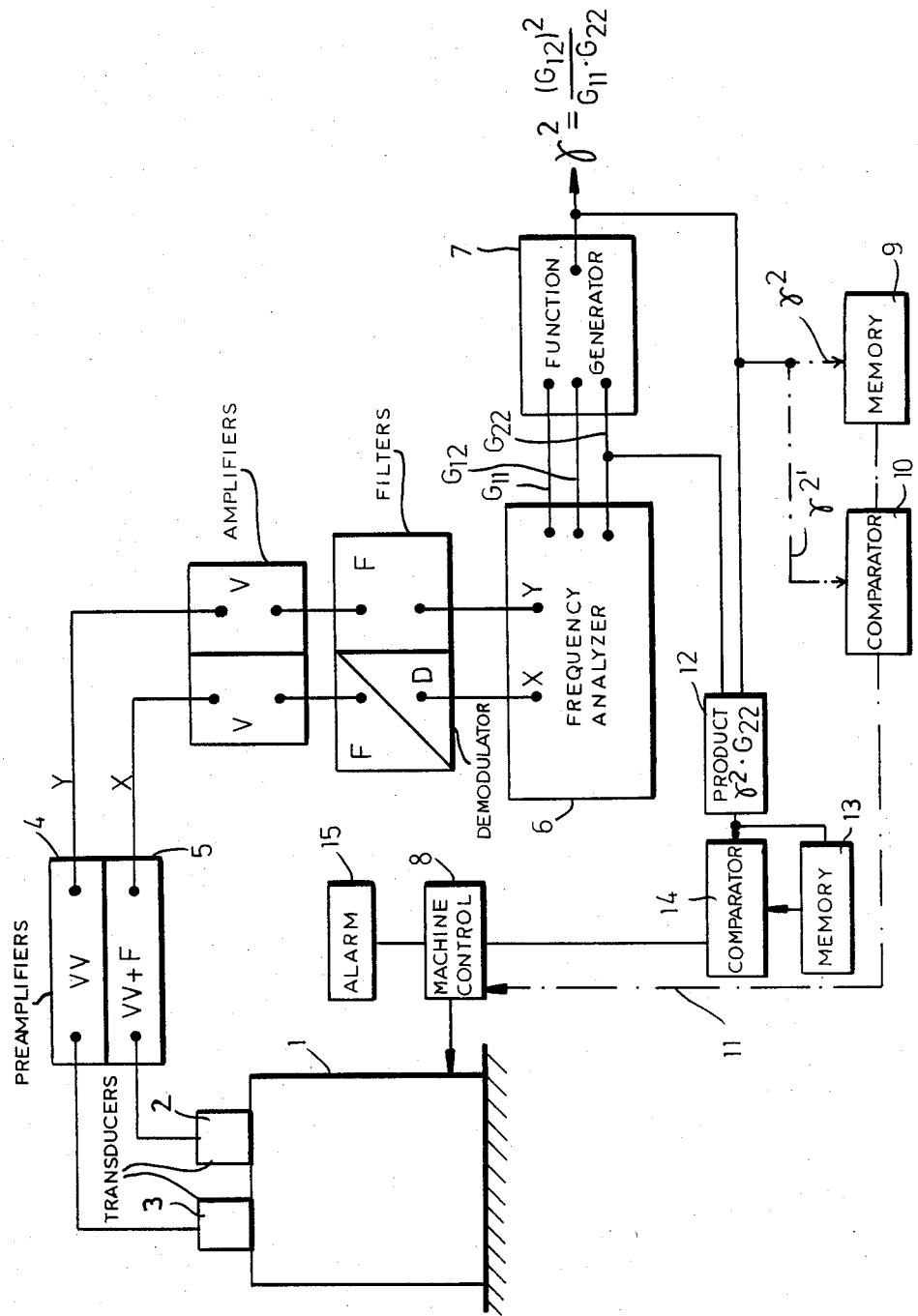

METHOD OF ANTICIPATING MACHINE FAILURE

FIELD OF THE INVENTION

My present invention relates to a method of anticipating machine failure, e.g. for cutting off machine operation in anticipation of machine failure, utilizing vibratory, acoustic or body waves which can be picked up from a machine part and which are generated during machine operation, especially for rotary machine parts.

BACKGROUND OF THE INVENTION

It is known that the body waves, generally in the acoustic or ultrasonic range generated in body parts of a machine, especially a rotating machine or a machine having a rotating element, can be utilized as a signal of a defect in the operation.

It is known, for example, to utilize transducers or pickups responsive to the wave energy in a machine body to measure a first body-wave parameter in a high-frequency range and a second body-wave parameter in a low-frequency range of the frequency spectrum generated upon machine operation and to compare the signals representing the picked up wave components in a comparator.

The comparator may be or can include a computer.

A process of this type is effectively used to monitor vibration in machine parts and, for example, for monitoring the conditions of bearings, transmission and turbine sets.

When the monitoring shows a change from a prior condition, this can represent a failure of the part or some other part associated with the machine.

The change in the oscillatory state or condition to which the device must respond, however, requires comparatively little energy so that the defect may be ascertained even upon startup.

The body-wave parameter which is measured directly or indirectly can be a function of the effective value of the acceleration, can be the first integral of this acceleration, i.e. the oscillation speed or velocity and/or the second integral of this acceleration or the first integral of the oscillation velocity, i.e. the displacement, lateral deflection or path deviation.

The measurements can be taken by appropriate transducers and subjected, with conventional frequency analyzers, to analysis, transformation and various forms of combination.

In one conventional technique (see *Olhydraulik und Pneumatik*, 1981, P. 568–573), the first body-wave parameter and the second body-wave parameter are measured in the same range of the frequency spectrum and at different times. The first body-wave parameter is measured when the machine and therefore the part to be monitored are newly in operation so that the first body-wave parameter can be constituted a reference value or can generate a reference value which is stored for later use. At a later time, this reference value is compared to the second body-wave parameter or a signal generated thereby or associated therewith and a deviation of the measured value from the reference value can be ascertained as an indication of failure.

It is also possible to utilize two body-wave parameters for this purpose, the first body-wave or reference parameter being measured at one frequency range of the body-wave spectrum while the second is measured at another frequency range. One of these frequency ranges may be a comparatively high frequency while the other frequency range may be a comparatively low frequency.

Since the second measurement of the body-wave parameter is not simultaneous or concurrent with the first or reference parameter, the measurement is not coherent. Coherency, as this term is used herein, refers to the ability to generate correlation relationships by spectral analysis, i.e. correlation between the phases of sperimposed waves generally with random variables arising from stochastic processes. Coherency with respect to waves is related to the tendency to generate interference interactions.

While these earlier techniques have proved to be satisfactory for many purposes, they have the important drawback that the measurements are only pertinent to a specific machine under specific conditions. Neither reference value measurement nor the second measurement at a later point in time can be utilized from one machine to the next even with mass produced or serially built machines which are of similar or identical construction. All of the values and calculations, therefore, must be done utilizng pickups on the respective machines at startup and operation.

The measurements, moreover, do not automatically allow anticipation of a defect state. This is because the frequency spectra are strongly dependent on the operating conditions and hence monitoring under conditions which vary with time is difficult, if not impossible, with conventional techniques.

For example, in a rotating machine which must operate at different speeds not only must measurement be taken to serve as a reference value in each machine of the class, but for each of the range of speeds at which the machine may operate if an accurate evaluation of the development of a defect state is to be ensured.

OBJECTS OF THE INVENTION

Accordingly it is the principal object of this invention to provide an improved method of monitoring the operation of a machine, especially a rotating machine, whereby these disadvantages are avoided.

Another object of the invention is to provide a method which will allow anticipation of a failure or defect state independently of any prior determination of reference values for a particular machine and even for an entire class of machines.

It is also an object of this invention to provide a system which allows the method to be carried out.

SUMMARY OF THE INVENTION

These objects and others which will become apparent hereinafter are attained in accordance with the invention in a method in which at least one wave pickup (transducer) picks up a first body-wave parameter from a part of an operating machine, preferaby a rotating machine, in a high-frequency range of the body-wave frequency spectrum while the same or another pickup responds to a second body-wave parameter in a low-frequency range of the frequency spectrum and the resulting signals are supplied to a frequency analyzer which generates from the measured value of the first body-wave parameter an auto-spectral density function $G_{11}$, also referred to as an auto-spectral power density function or auto-power spectrum, while from the measured value of the second body-wave parameter an auto-spectral power density function $G_{22}$ or auto-power spectrum is generated while from the two measured values of the body-wave parameter, the cross spectral density function $G_{12}$ is formed, the latter also being referred to as the cross power spectrum.

These spectral density functions $G_{11}$, $G_{22}$ and $G_{12}$ are then supplied to a computer or other unit having an appropriate transfer function so as to form the coherence function $\gamma^2$, i.e. a transfer function which provides the square of the value $G_{12}$ and divides that square by the product of the values $G_{11}$, $G_{22}$.

According to the invention, the coherence function $\gamma^2$ as thus measured, e.g. continuously during operation of the machine or at intervals in the life of machine operation is monitored and an increase in the value of $\gamma^2$ is recognized as an indication of future failure, i.e. represents the anticipated failure of the part.

According to the invention, one can operate directly or indirectly with the coherence function $\gamma^2$ so that the machine is cut off, for example, when the $\gamma^2$ measurement at any point in time compared to any prior point in time increases. It is, however, also possible to form the product of the coherence function with the second auto-spectral density function, $G_{22}$, i.e. the magnitude $\gamma^2 G_{22}$ and to utilize an increase in this value as the failure anticipation signal which is used to cut off operation of the machine.

It will be understood that, in accordance with the invention the comparison of the high-frequency and low-frequency signals by means of the coherence function must be effected at a given frequency. The high-frequency signal is thus demodulated so that by the demodulation the carrier frequency of the high-frequency signal, for example 200 kHz is suppressed while the low-frequency amplitude modulation remains. The demodulated high-frequency signal is then transformed into a low-frequency signal. The demodulator required for this purpose can be a commercially available demodulator as is used in radio receivers.

The auto-spectral density function and the cross spectral density function can be derived in a manner conventional in random data analysis, for example, as described in Bendat, Piersol *Engineering Applications of Correlation and Spectral Analysis*, John Wiley & Sons, 1980. Particular reference may be made to pages 50 ff where auto and cross spectral density functions are described, it being understood that one-sided functions are used in accordance with the invention. This work also describes the generation of the functions $G_{11}$, $G_{22}$ and $G_{12}$ so that the means there utilized may be employed here as well.

A surprising result of the present invention is that it is not necessary to determine reference values during the initial run in operations of a machine. Any machine operating in its normal or nondefective state can be monitored and the increase in the value of the coherence function $\gamma^2$ utilized to signal a future defect. In other words before there is a detrimental change in the value of $\gamma^2$, there is a correlation between the values as determined by the coherence function and the latter remains constant. When, however, there is an incipient defect, this is reflected in an increased value of $\gamma^2$ and a more pronounced increase in the value of the product of $\gamma^2$ with $G_{22}$ so that this change can be readily detected and utilized as a basis for cutting off machine operation or initiating change of parts, replacement of portions of a machine or repair.

The computer can be a conventional computer of the type utilized for correlation research.

BRIEF DESCRIPTION OF THE DRAWING

The above and other objects, features and advantages of the present invention will become more readily apparent from the following description, reference being made to the accompanying drawing, the sole FIGURE of which is a block diagram illustrating an apparatus for carrying out the invention.

SPECIFIC DESCRIPTION

In the drawing I have shown a machine 1, usually a rotating machine, capable of generating body waves during the course of operation. The machine may be a turbine, a transmission, a motor, a pump or any other machine which produces periodic vibrations or oscillations which are transmitted through a body part in the form of wave energy. Such wave energy is referred to herein as body waves to distinguish it from waves which are transmitted otherwise than through the solid material forming a machine part.

The first pickup or transducer 2, which may be an acoustic/electrical transducer, such as a piezoelectric transducer, measures a first body-wave parameter in a high-frequency range of the body-wave frequency spectrum.

Another pickup 3 of similar mechanical/electrical type can pick up a second body-wave parameter at the low-frequency range of this body-wave spectrum.

The two measured values are analyzed in a frequency analyzer 6 which can form part of a computer. To this end, the outputs of the transducers 2 and 3 are applied to preamplifiers VV shown at 4 and 5, the latter of which is also provided with a filter represented at F. The respective magnitudes shown at X and Y, vary with time, are fed via amplifiers V and through respective filters which can be narrow-band filters, one of which may be provided with a demodulator D as previously described, to the frequency analyzer. The latter generates the one-sided values $G_{11}$ of the auto-spectral density function of the high-frequency branch X, the auto-spectral density function $G_{22}$ of the low frequency branch Y and the cross spectral density function $G_{12}$ from the product of the two latter values $G_{11}$ and $G_{22}$. (See pages 54 and 55 of *Engineering Applications of Correlations and Spectral Analysis* cited above.)

These values of the respective spectra are applied to a function generator 7 which produces the square of the value $G_{12}$ and the bottom of the values $G_{11}$ and $G_{22}$ to generate the quotient $\gamma^2 = G_{12}^2 / G_{11} \cdot G_{22}$.

As can be seen from the drawing moreover, the machine can be provided with a machine control 8 capable of cutting off machine operation upon anticipation of an impending defect state. The machine cutoff control 8 can be triggered by an increase in the value of $\gamma^2$. This is achieved by applying the value of $\gamma^2$ to a memory 9 which records an instantaneous value of $\gamma^2$ and retains this value for a brief period of time sufficient to enable it to be applied to a comparator 10 together with a current value of $\gamma^2$. The result of this comparison is a signal applied via line 11 to the machine control 8 representing an increased value of $\gamma^2$ by comparison to a prior value of $\gamma^2$ exceeding a certain threshold.

Alternatively, I may form a product $\gamma^2 \cdot G_{22}$ in a multiplier 12 and store briefly the output of this multiplier in a memory 13 so that the latter can be compared with a later value of the product in a comparator 14 to trigger the machine control 8 and an alarm 15 representing impending machine failure.

I claim:

1. In a method of operating a machine producing body waves in a machine part and in which a measurement is made of a first body-wave parameter at a relatively high-frequency range of a frequency spectrum of said body waves and a second body-wave parameter is measured in a low-frequency range of said frequency spectrum, the improvement which comprises:
   generating an auto-spectral density value $G_{11}$ corresponding to the measurement of said first parameter;
   generating a second auto-spectral density value $G_{22}$ from said measurement of said second body-wave parameter;
   generating a cross spectral density value $G_{12}$ from both of the measurements;
   automatically forming the coherence function $\gamma^2 = G_{12}{}^2/G_{11} \cdot G_{22}$; and
   detecting an increase in the value of $\gamma^2$ as an anticipation of impending failure of said machine.

2. The improvement defined in claim 1, further comprising the step of cutting off operating of said machine upon a rise in the value of $\gamma^2$.

3. The improvement defined in claim 1, further comprising the step of generating a product $\gamma^2 \cdot G_{22}$ and detecting an increase in the value of said product as representing anticipatory failure of said machine.

4. The improvement defined in claim 1, further comprising the step of terminating operation of said machine upon an increase in said product.

5. In a system for monitoring a machine generating body waves in operation for anticipation of failure of said machine, wherein a first body-wave parameter is measured on said machine in a relatively high-frequency range of a frequency spectrum of said body waves and a second body-wave parameter is measured on said machine at a relatively low frequency of said frequency spectrum, the improvement which comprises:
   means for deriving respective high-frequency and low-frequency values from said measurements;
   a frequency analyzing computer connected to said means for generating from said values an auto-spectral density function $G_{11}$ from said high-frequency value, a second auto-spectral density function $G_{22}$ from said low-frequency value, and a cross spectral density function $G_{12}$ from both values; and
   a function generator connected to said computer for generating the function $\gamma^2 = G_{12}{}^2/G_{11} \cdot G_{22}$, where an increase in the value of $\gamma^2$ anticipates a defect in said machine.

6. The system defined in claim 5, further comprising means responsive to an increase in a value of $\gamma^2$ for automatically cutting off operation of said machine.

7. The system defined in claim 5 wherein the means for generating said high-frequency value includes a demodulator.

* * * * *